United States Patent
Chan et al.

(10) Patent No.: US 9,823,191 B2
(45) Date of Patent: Nov. 21, 2017

(54) MICRO-PRISM TEST CHIP

(71) Applicants: Benny L. Chan, Fremont, CA (US); Suganda Jutamulia, Berkeley, CA (US)

(72) Inventors: Benny L. Chan, Fremont, CA (US); Suganda Jutamulia, Berkeley, CA (US)

(73) Assignee: Ecolife Technologies, LLC, Fremont, CA (US)

( * ) Notice: Subject to any disclaimer, the term of this patent is extended or adjusted under 35 U.S.C. 154(b) by 0 days.

(21) Appl. No.: 14/120,049

(22) Filed: Apr. 19, 2014

(65) Prior Publication Data

US 2015/0300954 A1  Oct. 22, 2015

(51) Int. Cl.
*G01N 21/29* (2006.01)
*G01N 21/552* (2014.01)

(52) U.S. Cl.
CPC .................................. *G01N 21/553* (2013.01)

(58) Field of Classification Search
CPC ......... G01N 21/554; G01N 2021/5903; G01N 21/55; G01N 21/4133; G01N 21/553; G02B 5/008; G02B 5/0231
USPC ....................................................... 422/82.05
See application file for complete search history.

(56) References Cited

U.S. PATENT DOCUMENTS

| | | | | |
|---|---|---|---|---|
| 6,420,984 B1 * | 7/2002 | Robertson | ............... | H03M 1/32 341/137 |
| 6,594,018 B1 * | 7/2003 | Bartholomew | ...... | G01N 21/553 356/445 |
| 7,197,196 B2 * | 3/2007 | Lin | ....... | G01N 21/553 356/445 |
| 7,465,588 B2 * | 12/2008 | Muraishi | ............. | G01N 21/553 385/12 |
| 2005/0087442 A1 | 4/2005 | Elkind | | |
| 2006/0274434 A1 * | 12/2006 | Mino | .................. | G02B 6/4214 359/811 |
| 2010/0061892 A1 * | 3/2010 | Flaim | .................. | B01J 19/0046 422/68.1 |
| 2011/0075976 A1 * | 3/2011 | Sutherland | ............. | G02B 6/423 385/88 |
| 2011/0128548 A1 | 6/2011 | Chinowsky et al. | | |
| 2011/0215705 A1 | 9/2011 | Long et al. | | |
| 2011/0310394 A1 | 12/2011 | Li | | |
| 2013/0078146 A1 * | 3/2013 | Sando | .................. | G01N 21/648 422/69 |

* cited by examiner

*Primary Examiner* — Monzer R Chorbaji
(74) *Attorney, Agent, or Firm* — Suganda Jutamulia

(57) ABSTRACT

A disposable micro-prism test chip for surface plasmon resonance measurement comprises a micro-tray and a micro-prism mounted on the micro-tray. The micro-tray and the micro-prism form at least one cell for providing a fluid dielectric medium for measurement. The disposable micro-prism test chip also comprises a thin metal layer coated on the surface of the micro-prism in the formed cell between the fluid dielectric medium and the micro-prism. The micro-tray may have at least one through window for forming the at least one cell. The micro-tray may also have a half-through cavity facing the micro-prism. The disposable micro-prism test chip is disposed after at least one use. The micro-prism may be fabricated by pulling a heated preform, where the preform has the same cross-section as that of the pulled micro-prism.

17 Claims, 12 Drawing Sheets

Top View

Bottom View

MICRO-PRISM TEST CHIP

FIELD OF THE INVENTION

This invention relates to a micro-prism test chip to be used in a surface plasmon resonance biosensor that is capable of measuring the refractive index of a fluid.

BACKGROUND OF THE INVENTION

Surface plasmon resonance (SPR) affinity biosensor relies on the measurement of the molecular binding induced refractive index changes and therefore it is label-free technology. Due to its high sensitivity, selectivity, and real-time measurement capability, SPR biosensor has become the technology of choice for researchers within the pharmaceutical and biomedical industry to characterize molecular interaction kinetic, thermodynamics, and concentration. SPR biosensors can support an incredible range of applications from qualitative binding to high resolution kinetic analysis. Nearly any interaction involving biological systems including low molecular weight components, proteins, nucleic acids, antibody, and even lipid surface environments are amenable to these instruments.

The SPR based technology continues to expand and improve to become an indispensable analytical tool in biomedical research. Although a tremendous progress has been made in modern days SPR equipment, SPR equipment is mostly based on bulky optics. Portable miniaturized SPR equipment with low cost disposable part is still in demand.

SUMMARY

In accordance with one embodiment, an apparatus comprises a disposable micro-prism test chip. The disposable micro-prism test chip may comprise a micro-tray and a micro-prism mounted on the micro-tray. The micro-tray and the micro-prism form at least one cell for providing a fluid dielectric medium for measurement. The disposable micro-prism test chip also comprises a thin metal layer coated on the surface of the micro-prism in the cell between the fluid dielectric medium and the micro-prism. The micro-tray may have at least one through window for forming the at least one cell. The micro-tray also may have a half-through cavity facing the micro-prism. The micro-tray may be a silicon tray singulated from a silicon wafer, a plastic molded tray, or a metal tray. The micro-prism may be fabricated by pulling a heated preform, where the preform has the same cross-section as that of the pulled micro-prism. The micro-prism may have a cross-section of equilateral triangle having a side less than 5 mm and a length less than 10 mm.

The apparatus further comprises a laser emitting TM wave laser light, a spherical lens for reducing divergence of the emitted laser light, a cylindrical lens for focusing the emitted laser light, and a detector for detecting laser light reflected by the surface of the micro-prism coated with the thin metal layer. The cylindrical lens may focus the emitted laser light at the proximity of the surface of the micro-prism coated with the thin metal layer. The micro-prism may be mounted on the silicon tray before or after the silicon tray is singulated from the silicon wafer. The micro-prism may be mounted on the silicon tray using adhesive. The thin metal layer may be coated on the surface of the micro-prism before or after the micro-prism is mounted on the micro-tray. The thin metal layer may be a thin gold, silver, aluminum, or copper layer.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Figure 1:
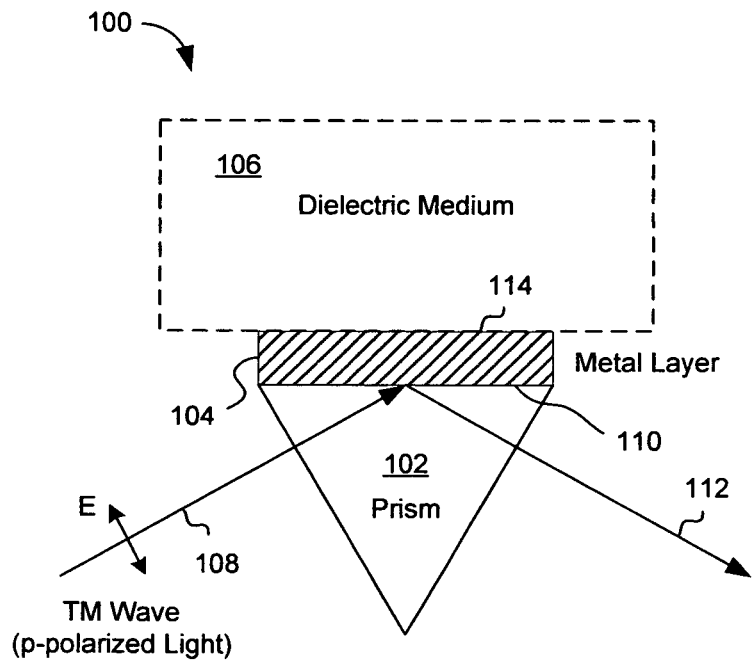
FIG. 1 shows an embodiment of the Kretschmann configuration using prism coupling to generate SPR.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable combinations and/or sub-combinations in one or more embodiments.

Kretschmann Configuration

FIG. 1 shows an embodiment 100 of the Kretschmann configuration using prism coupling to generate SPR. Embodiment 100 of the Kretschmann configuration typically comprises a bulky glass prism 102. A side of glass prism 102 is coated with a thin metal layer 104. For example, thin metal layer 104 may have a thickness of about 50 nm. Thin metal layer 104 is in direct contact with a dielectric medium 106 of lower refractive index. The dielectric medium may be a fluid. When a TM wave (p-polarized) light beam 108, is incident through prism 102 on a prism metal interface 110, the incident beam 108 is reflected to be a reflected beam 112. When an incident angle θ of incident beam 108 is larger than the critical angle between prism 102 and dielectric medium 106 without thin metal layer 104, an evanescent wave is produced perpendicular to prism metal interface 110. The evanescent wave propagates from prism 102 into dielectric medium 106 through thin metal layer 104 and decays exponentially. The evanescent wave is characterized by incidence angle θ of incident beam 108 and the dielectric constant of prism 102.

The surface plasmon wave (SPW) is a TM electromagnetic wave which propagates at an interface 114 between dielectric medium 106 and thin metal layer 104. The SPW is characterized by the dielectric constants of thin metal layer 104 and the dielectric constant of dielectric medium 106. At a particular resonance incidence angle, θ-resonance, of incident beam 108, the energy of the evanescent wave is transferred to excite the SPW. Accordingly, the intensity of reflected beam 112 is reduced when the energy of incident beam 108 is transferred to the SPW through the evanescent wave.

Figure 2:
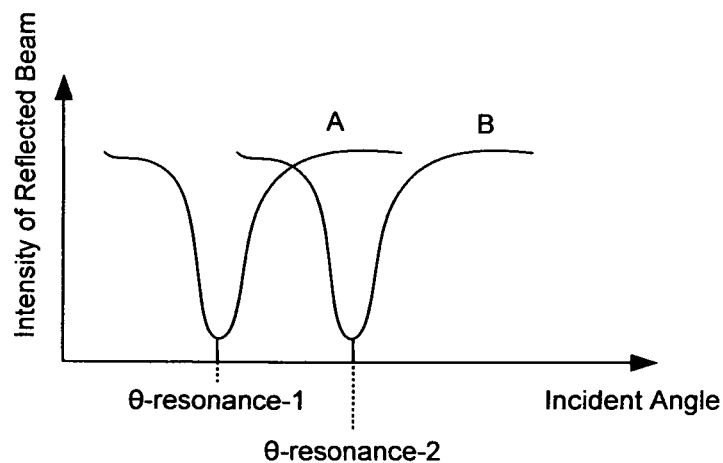
FIG. 2 shows the intensity of the reflected beam as function of the incident angle θ.

FIG. 2 shows the intensity of reflected beam 112 as function of incident angle θ. At the resonance condition, there is transfer of energy from incident beam 108 to SPW propagating at interface 114 resulting in a reduction of intensity of reflected beam 112. The intensity of reflected beam 112 of curve A shows a sharp dip at resonance angle θ-resonance-1. The value of θ-resonance-1 can be determined from curve A, which may be obtained from measurement. If the dielectric constants of prism 102 and thin metal layer 104 are known, the dielectric constant of dielectric medium 106 can be determined. Thus the dielectric constant and also the refractive index of dielectric medium 106 in contact with thin metal layer 104 can be determined. Furthermore, when the refractive index of dielectric medium 106 changes, the reflectance dip shifts to another angle accordingly. For example curve A shifts to curve B, θ-resonance-1 shifts to θ-resonance-2. If the refractive index of a fluid is related to the concentration of a component in the fluid, the concentration of the component can be determined as well.

Fabrication of Micro-Prism

In an embodiment according to the present invention, bulky glass prism 102 of FIG. 1 is replaced with a micro-prism, which is fabricated by a special technique similar to a glass fiber drawing technique. The micro-prism serves as a part of a disposable test chip. In the conventional approach, the disposable test chip and prism are two separate components, the bulk prism is built in to the equipment and the disposable test chip is usually a piece of glass slide with processed bio-specific element on the top surface. The disposable test chip, e.g., glass slide, is attached to the bulk prism with index matching fluid and will be discarded after a single or multiple uses. In an embodiment according to the present invention, there is no disposable glass slide. The micro-prism is disposable. Since no glass slide test chip is required, the need of using index matching fluid will be eliminated and the switching between tests will be easy.

The fabrication method for micro-prism is similar to the glass fiber drawing technique. Due to the nature of this glass drawing technique, because it includes cross-sectional size reduction and fire polish, the drawn micro-prism exhibits very high quality surface finish without any subsequent grinding and polishing. Thus the cost may be tremendously low.

There are three major advantages of drawing micro-prism: (1) no initial or subsequent mold cost is required, (2) the precision and product uniformity is excellent, and (3) the combination geometry reduction and fire polishing nature of this process produces very high quality diffraction limited surface finish that may improve the quality of SPR measurement result.

Figure 3:
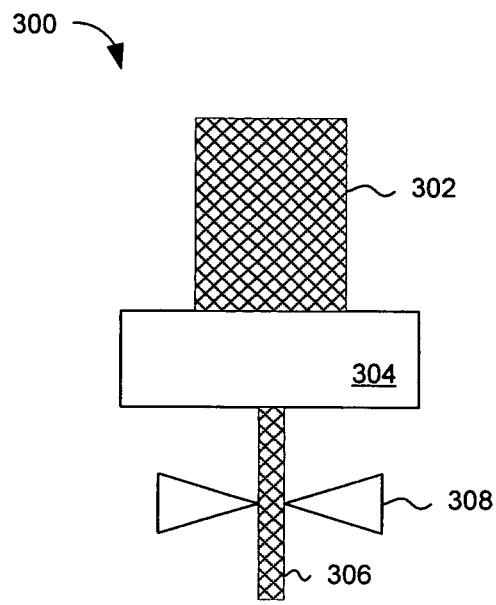
FIG. 3 shows an exemplary process for drawing micro-prism according to the present invention.

The process involves a drawing tower similar to that for optical fiber production as shown in FIG. 3. FIG. 3 shows an exemplary process 300 for drawing micro-prism according to the present invention. The drawing process is relatively straightforward. A glass preform 302 having a shape of prism is suspended vertically above a furnace 304 or oven and lowered slowly. Once inside the heat zone, the lowest part of glass preform 302 softens and is pulled from below at a rate exceeding that of the feed into furnace 304 depending on the desired cross-sectional size reduction. The proper pull rate can be calculated based on the feed rate and the conservation of mass in and mass out. Furnace 304 may be temperature controlled. The size of micro-prism 306 may be in-situ close loop controlled by a laser micrometer 308 during the pulling. A drawn micro-prism 306 is segmented to an appropriate length. The preform may be made of glass or other materials that can be pulled at an elevated temperature.

Figure 4:
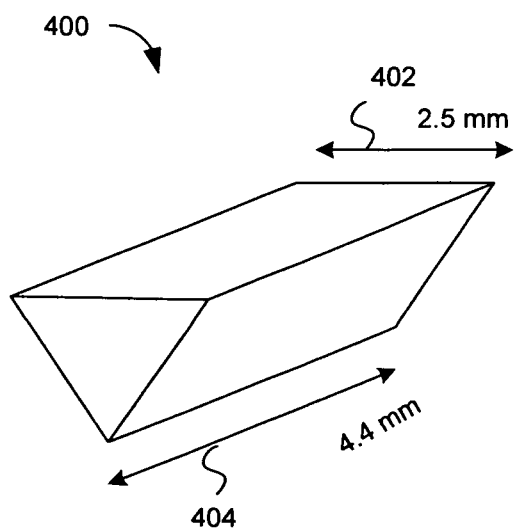
FIG. 4 shows an exemplary geometry of a drawn equilateral triangular micro-prism according to the present invention.

FIG. 4 shows an exemplary geometry of a fabricated equilateral triangular micro-prism 400, according to the present invention. Each side of micro-prism 400 may be approximately 2.5 mm. The length of micro-prism 400 may be approximately 4.4 mm for a test chip. In an embodiment, the side of micro-prism may be less than 5 mm. In another embodiment, the length of micro-prism may be less than 10 mm. It is appreciated that other shapes and dimensions are possible. One side surface of micro-prism 400 is coated with a thin metal layer, for example, the metal may be gold, silver, aluminum, copper, or other suitable metals. In an embodiment, a bulk prism may be used instead of the drawn micro-prism.

Laser Line Generator

Figure 5A:
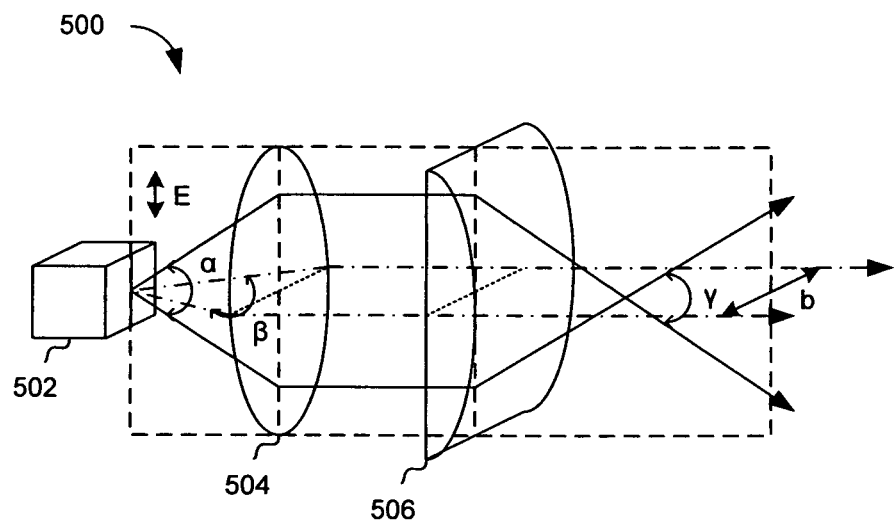
FIG. 5A shows a laser line generator according to the present invention.

FIG. 5A shows a laser line generator 500 according to the present invention. Laser line generator comprises a laser diode (semiconductor laser) 502 that emits a TM wave (p-polarized) laser light having short-axis divergent angle α and long-axis divergent angle $\beta$. The emitted laser light is collimated by a collimating lens 504. The collimated light passes a cylindrical lens 506 that spreads the light along the short axis with a divergent angle $\gamma$, while keeps the light collimated along the long axis with a thickness of b. Thus, a fan-shape light sheet with divergent angle $\gamma$ and thickness b may be formed. Other laser line generators are possible as shown in FIGS. 5B and 5C.

Figure 5B:
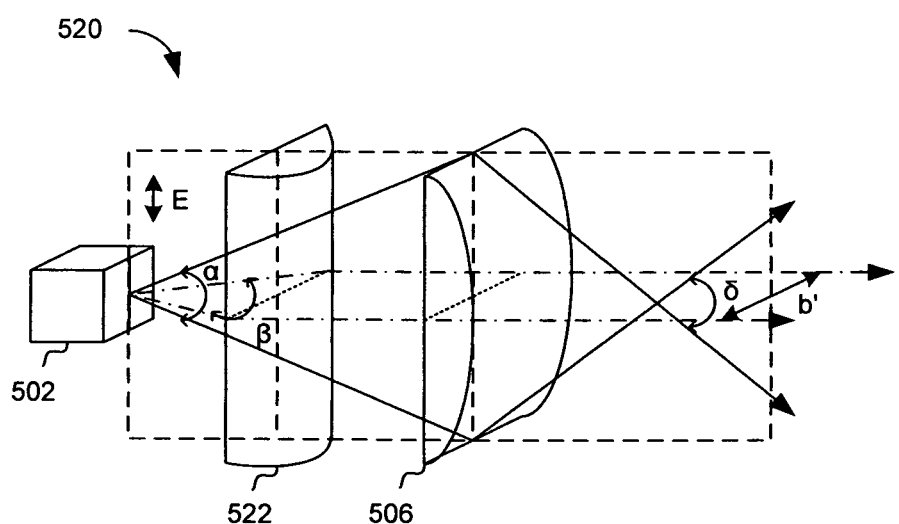
FIG. 5B shows a laser line generator according to the present invention.

FIG. 5B shows a laser line generator 520 according to the present invention. Laser line generator 520 uses a cylindrical lens 522 replacing collimating lens 504 of FIG. 5A. Cylindrical lens 522 collimates the emitted laser beam along the long axis with a thickness b'. Cylindrical lens 522 does not change the short-axis divergent angle $\alpha$. Cylindrical lens 506 changes the short-axis divergent a to a divergent angle $\delta$. Cylindrical lens 506 does not change the beam along the long axis. A fan-shape light sheet with divergent angle $\delta$ and thickness b' may be formed.

Figure 5C:
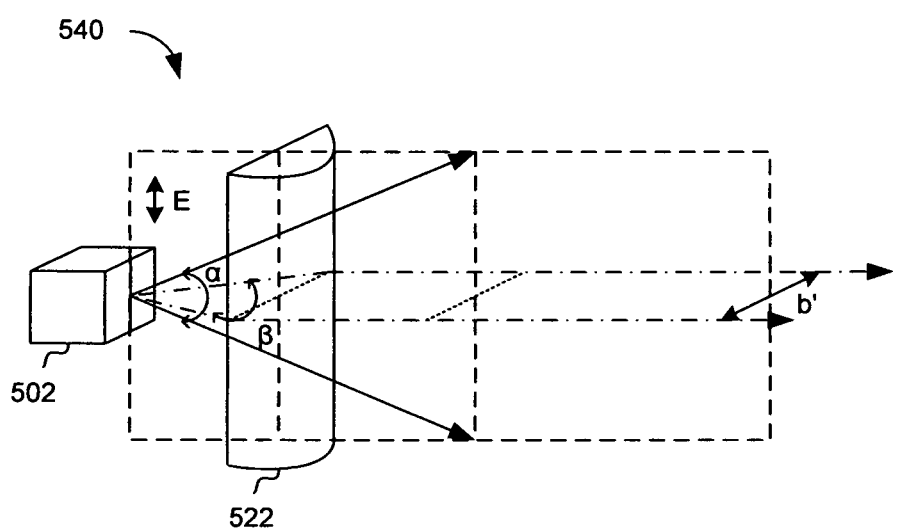
FIG. 5C shows a laser line generator according to the present invention.

FIG. 5C shows a laser line generator 540 according to the present invention. Laser line generator 540 uses cylindrical lens 522 only without collimating lens 504 and cylindrical lens 506 of FIG. 5A. A fan-shape light sheet with divergent angle $\alpha$, which is the short-axis divergent angle of the emitted laser beam, and thickness b' may be formed.

Optical Assembly

Figure 6A:
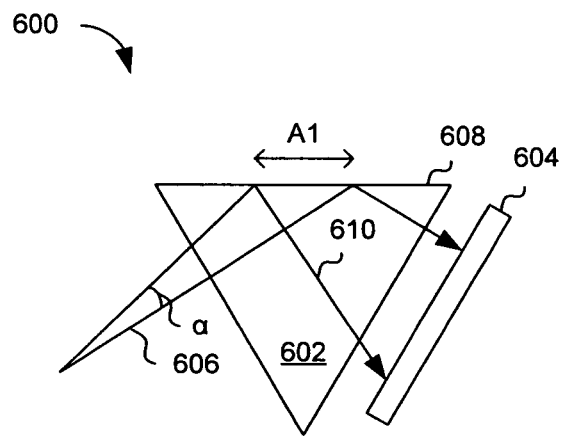
FIG. 6A shows an optical assembly comprising a micro-prism and a detector according to the present invention.

FIG. 6A shows an optical assembly 600 comprising a micro-prism 602 and a detector 604, according to the present invention. Detector 604 may be a 1D linear detector or a 2D array detector. A fan-shape laser light sheet 606 having a divergent angle $\alpha$ is incident on a side surface 608 of micro-prism 602. A light spot having a width A1 is formed on side surface 608 of micro-prism 602. A thin metal layer is coated on side surface 608. A fluid dielectric medium is disposed on the thin metal layer. The fluid dielectric medium may be a liquid solution or gas. A PSW is generated by incident beam 606 having a particular resonance incident angle. At the resonance incident angle, the intensity of a reflected beam 610 decreases. Detector 604 detects the intensity of reflected beam 610 at all incident angles within a range. Each element or pixel of detector 604 may correspond to an incident angle within the range.

Figure 6B:
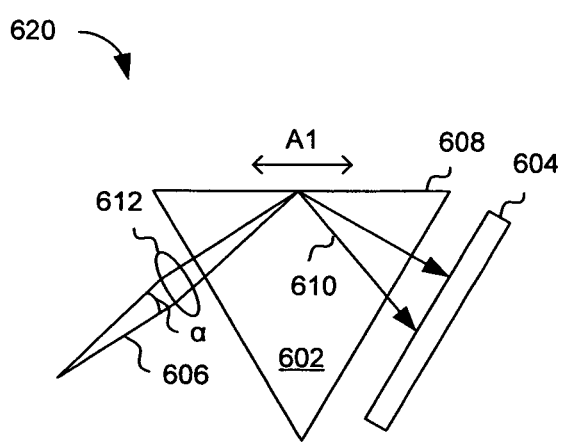
FIG. 6B shows an optical assembly comprising a micro-prism and a detector according to the present invention.
Figure 6C:
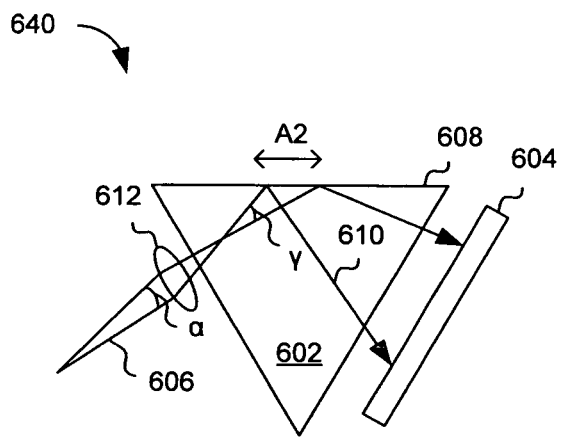
FIG. 6C shows an optical assembly comprising a micro-prism and a detector according to the present invention.

FIG. 6B shows an optical assembly 620 similar to optical assembly 600 of FIG. 6A, according to the present invention. The difference between optical assembly 620 and optical assembly 600 is that incident beam 606 is focused by a focusing lens 612 on side surface 608. Focusing lens 612 may be a cylindrical lens. FIG. 6C shows another optical assembly 640 similar to optical assembly 600 of FIG. 6A, according to the present invention. The difference between optical assembly 640 and optical assembly 600 is that incident beam 606 is focused by focusing lens 612 at the proximity of side surface 608 before or after (not shown) it reaches side surface 608. A fan-shape laser light sheet having a divergent angle $\gamma$ is incident on side surface 608 of micro-prism 602. A light spot having a width A2 is formed on side surface 608 of micro-prism 602.

Figure 6D:
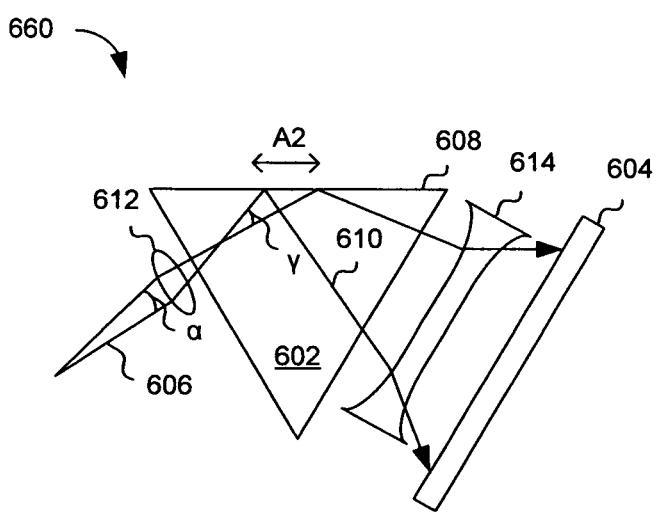
FIG. 6D shows optical assembly of FIG. 6C further comprising a diverging lens according to the present invention

FIG. 6D shows an optical assembly 660 similar to optical assembly 640 of FIG. 6C, according to the present invention. The difference between optical assembly 660 and optical assembly 640 is that it includes a diverging lens 614 to increase diverging angle $\gamma$ of reflected beam 610. Diverging lens 614 may be a cylindrical lens. In this manner, detector 604 may detect signals having better angular resolution. It is appreciated that optical assembly 600 of FIG. 6A and optical assembly 620 of FIG. 6B may include a diverging lens as well.

Figure 7:
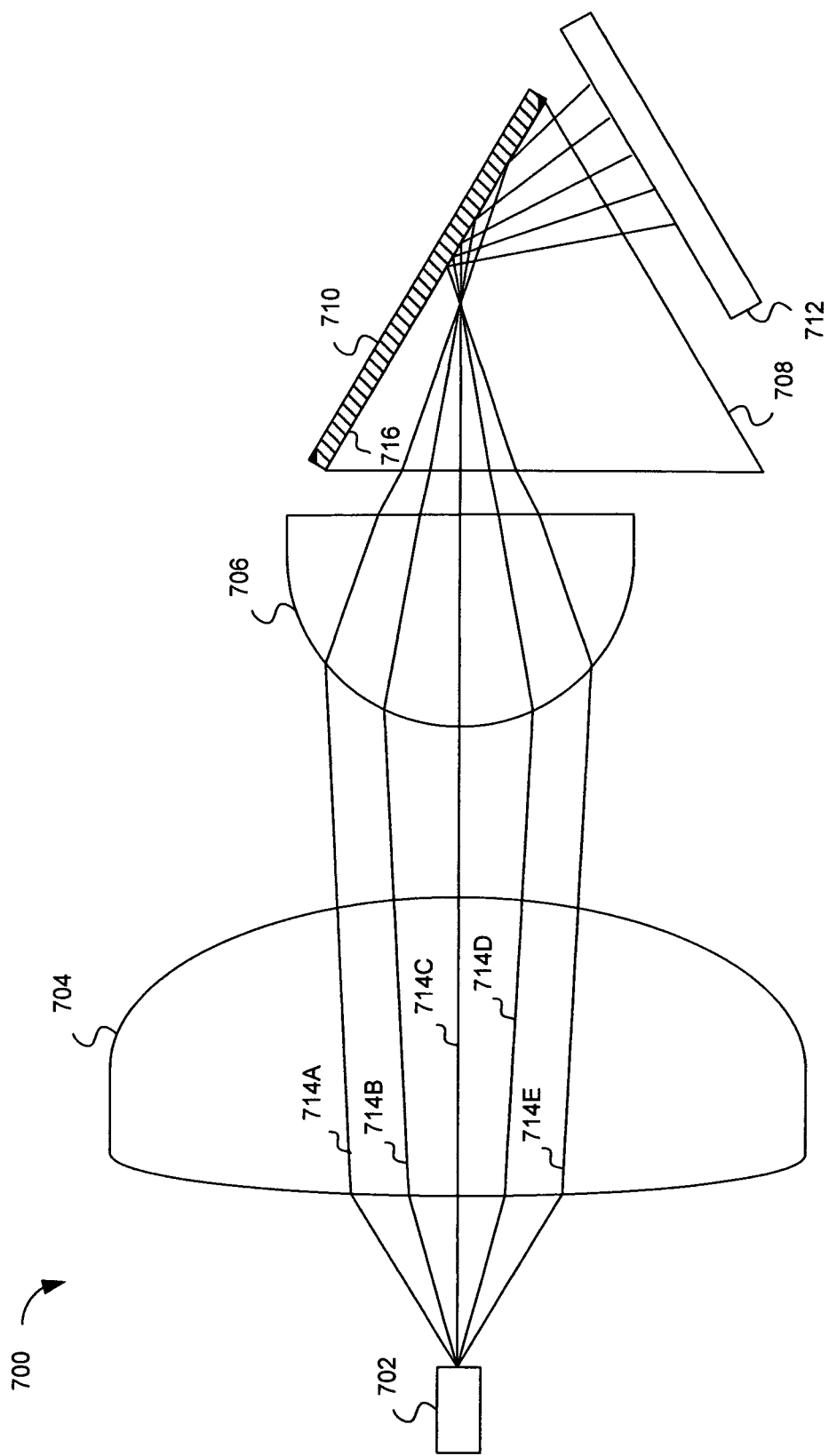
FIG. 7 shows an exemplary optical assembly comprising laser line generator of FIG. 5A and optical assembly of FIG. 6C according to the present invention.

FIG. 7 shows an exemplary optical assembly 700 comprising laser line generator 500 of FIG. 5A and optical assembly 640 of FIG. 6C, according to the present invention. Optical assembly 700 comprises a laser diode 702 emitting TM wave laser light, a spherical lens 704 for reducing the divergence of the emitted laser light, a cylindrical lens 706 for focusing the emitted laser light, a micro-prism 708 having a surface 716 coated with a thin metal layer 710, and a 2D array detector 712 for detecting laser light reflected by surface 716 of micro-prism 708 coated with thin metal layer 710. It is appreciated that reducing the divergence of the emitted laser light includes collimating the emitted laser light.

2D array detector 712 may be a CMOS image sensor. 2D array detector 712 may be any types of image sensor or any types of linear detector as well. Light paths 714A, 714B, 714C, 714D, and 714E are exemplary incident lights having different incident angles at the interface of micro-prism 708 and thin metal layer 710. Light paths 714A-714E are detected by different lines of elements or pixels of 2D array detector 712. As described previously, optical assembly 700 may also include a cylindrical diverging lens (not shown) between micro-prism 708 and detector 712 or in front of detector 712.

Disposable Micro-Prism Test Chip

Figure 8A:
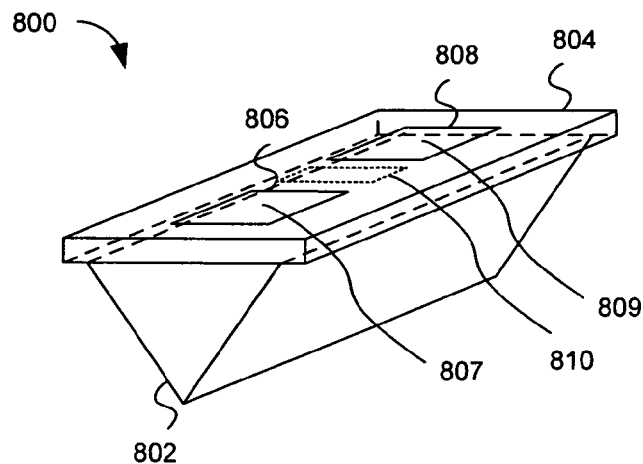
FIG. 8A shows an exemplary disposable micro-prism test chip according to the present invention.

FIG. 8A shows an exemplary disposable micro-prism test chip (MPTC) 800 according to the present invention. MPTC 800 comprises a micro-tray 804 and a micro-prism 802 mounted on micro-tray 804. Micro-tray 804 and micro-prism 802 form at least one cell 807 for providing a fluid dielectric medium for measurement. MPTC 800 also comprises a thin metal layer (not shown in FIG. 8A) coated on the surface of the micro-prism in cell 807 between the fluid dielectric medium and micro-prism 802. Micro-tray 804 may have at least one through window 806 for forming at least one cell 807. Micro-tray 804 may be a silicon tray. Micro-tray 804 may be a molded plastic tray or a metal tray as well.

For example, micro-tray 804 comprises a first through window 806 for forming a first or reference cell 807 on micro-prism 802, a second through window 808 for forming a second or sample cell 809 on micro-prism 802, a half-through cavity 810 facing micro-prism 802, and trenches 812 (not shown in FIG. 8A) facing micro-prism 802. Epoxy, glue, cement, or other adhesives may fill trenches 812 for mounting micro-prism 802 on micro-tray 804.

It is appreciated that micro-tray 804 may comprise only one through window forming only one cell or more than two through windows forming more than two cells as well. In an embodiment, micro-tray 804 comprises more than two through windows and MPTC 800 has more than two cells that may be used for multiple detections. In another embodiment, micro-tray 804 comprises only one through window forming only one cell. The surface of micro-prism 802 in the cell or cells is coated with a thin metal layer (not shown in FIG. 8A). For example, the metal may be gold, silver, aluminum, copper, or any suitable metal.

Figure 8B:
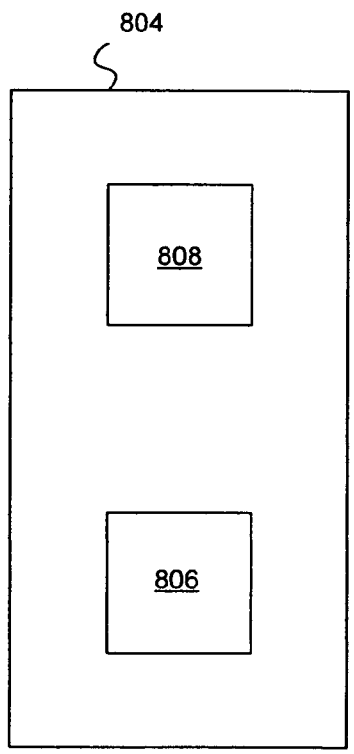
FIG. 8B shows schematically top view of an exemplary micro-tray according to the present invention.
Figure 8C:
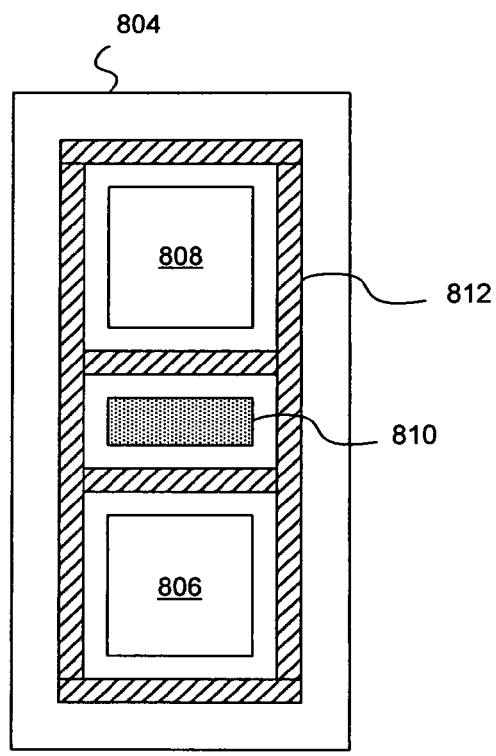
FIG. 8C shows schematically bottom view of an exemplary micro-tray according to the present invention.

FIG. 8B shows schematically a top view of exemplary micro-tray 804 according to the present invention. As seen from the top view, micro-tray 804 comprises first through window 806 and second through window 808. FIG. 8C shows schematically a bottom view of exemplary micro-tray 804 according to the present invention. As seen from the bottom view, in addition to first through window 806 and second through window 808, micro-tray 804 also comprises half-through cavity 810 and trenches 812. Half-through cavity 810 and trenches 812 may have the same etched depth, or may have different etched depth. Half-through cavity 810 and trenches 812 are facing micro-prism 802.

Adhesives may fill trenches 812, and micro-prism 802 may be mounted on micro-tray 804. It is appreciated that although a closed-loop pattern of trenches 812 is shown, an open-loop pattern of trenches 812 is possible, and in some instances it may be demanded, for example, for the overflow of filling adhesive. In other embodiments, other means may be used to mount micro-prism 802 on micro-tray 804 not using adhesive. The mounting means may include electrical, magnetic, mechanical, and other methods.

Figure 8D:
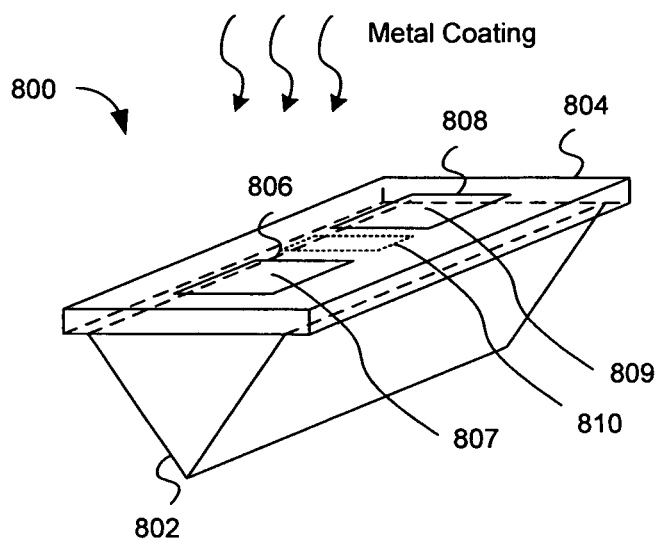
FIG. 8D shows the whole assembly coated with metal according to the present invention.

After micro-prism 802 is mounted on micro-tray 804, the top surface of the whole assembly is coated with metal, for example, gold, silver, aluminum, or copper as shown in FIG. 8D according to the present invention. In this manner, the surface of micro-prism 802 exposed by through windows 806 and 808 is coated with metal, while the surface of micro-prism 802 in half-through cavity 810 is not coated, since it is covered by micro-tray 804.

In an embodiment, a micro-prism test chip may comprise a pulled micro-prism alone. In another embodiment, the micro-prism test chip may further comprise a micro-tray of different designs. The micro-prism test chip may be disposable and may not be disposable.

Fabrication of Silicon Tray

Figure 9A:
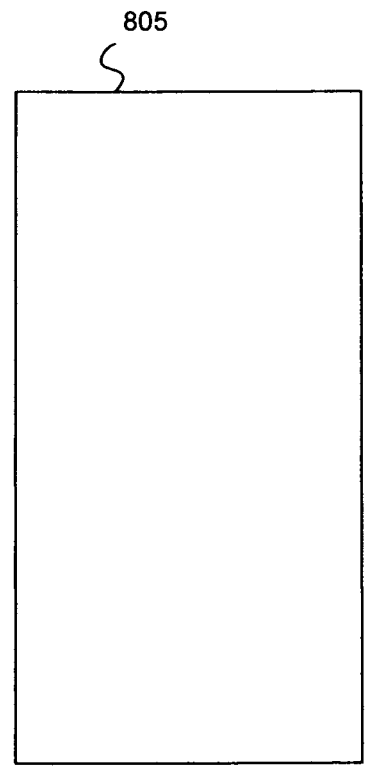
FIGS. 9A-9C show an exemplary process for forming a silicon tray according to the present invention.
Figure 9B:
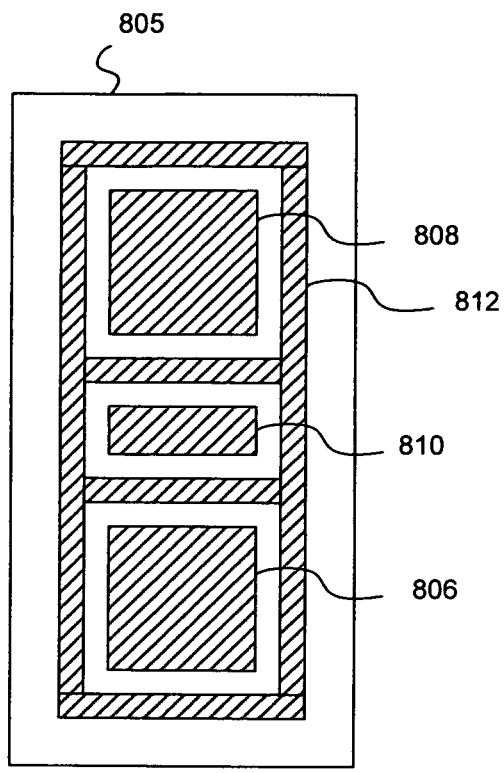
Figure 9C:
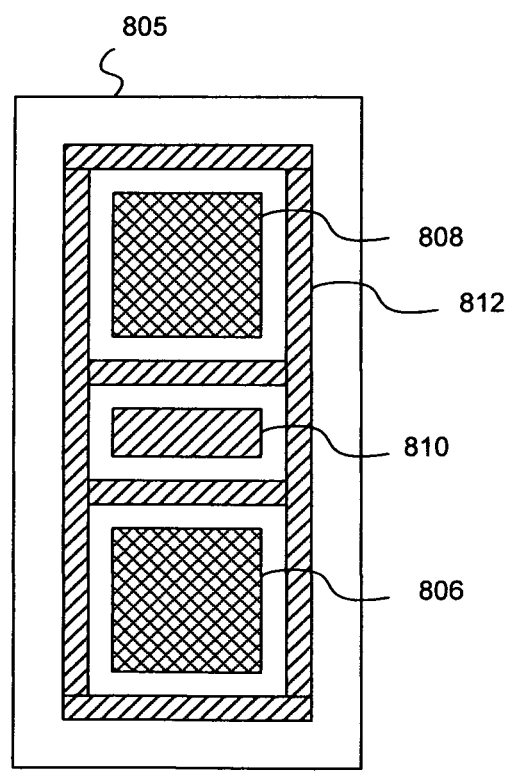

FIGS. 9A-9C show an exemplary process for forming a silicon tray 805 according to the present invention. FIG. 9A shows a silicon wafer 805 according to the present invention. For example, the thickness of silicon wafer 805 is 400 µm. In a first step, for example, a first through window 806, a second through window 808, a half-through cavity 810, and trenches 812 are etched for a depth 75 µm, which is less than the thickness of the wafer (400 µm). FIG. 9B shows the etched silicon wafer 805 after the first step according to the present invention. In a second step, for example, first through window 806 and second through window 808 are further etched through the wafer. FIG. 9C shows the etched silicon wafer 805 after the second step having first through window 806, second through window 808, half-through cavity 810, and trenches 812, according to the present invention.

It is appreciated that various processes are possible. For example, in the first step a half-through cavity and trenches only are etched. In the second step, the through windows are etched. For example, the two opposite surfaces of the silicon wafer are etched in the first step and second step, respectively. In another example, the same surface is etched in the first step and second step.

As described previously, a plastic tray similar to silicon tray 805 may be fabricated by molding, 3D printing, or other suitable processes. A metal tray similar to silicon tray 805 may be fabricated by etching, cutting, drilling, or other suitable processes as well.

Half-Through Cavity

The function of half-through cavity 810 is to provide calibration reference. The half-through cavity contains air. No metal layer is coated on the surface of micro-prism in half-through cavity 810. The critical angle is defined at the interface of prism and air. For example, the prism may be made of glass having an index of refraction of 1.5. The index of refraction of air is 1. Thus, the critical angle is 41.81° (sin 41.81°=1/1.5). If the incident angle at the interface is equal or larger than 41.81° it will be reflected, and if the incident angle is less than 41.81°, the incident light will leave the prism and will not be reflected. Accordingly, the boundary of the detected reflected light and undetected transmitted light at the detector corresponds to the critical angle, which may be used for calibration of the incident angle of reflected light at the detector.

The calibration reference may be provided by an SPR resonance angle as well. In this embodiment, the surface of micro-prism in half-through cavity 810 is coated with the same thin metal layer. The detected dark band will correspond to the SPR resonance angle, which may be used for calibration of the incident angle of reflected light at the detector.

Silicon Wafer Processing

Figure 10:
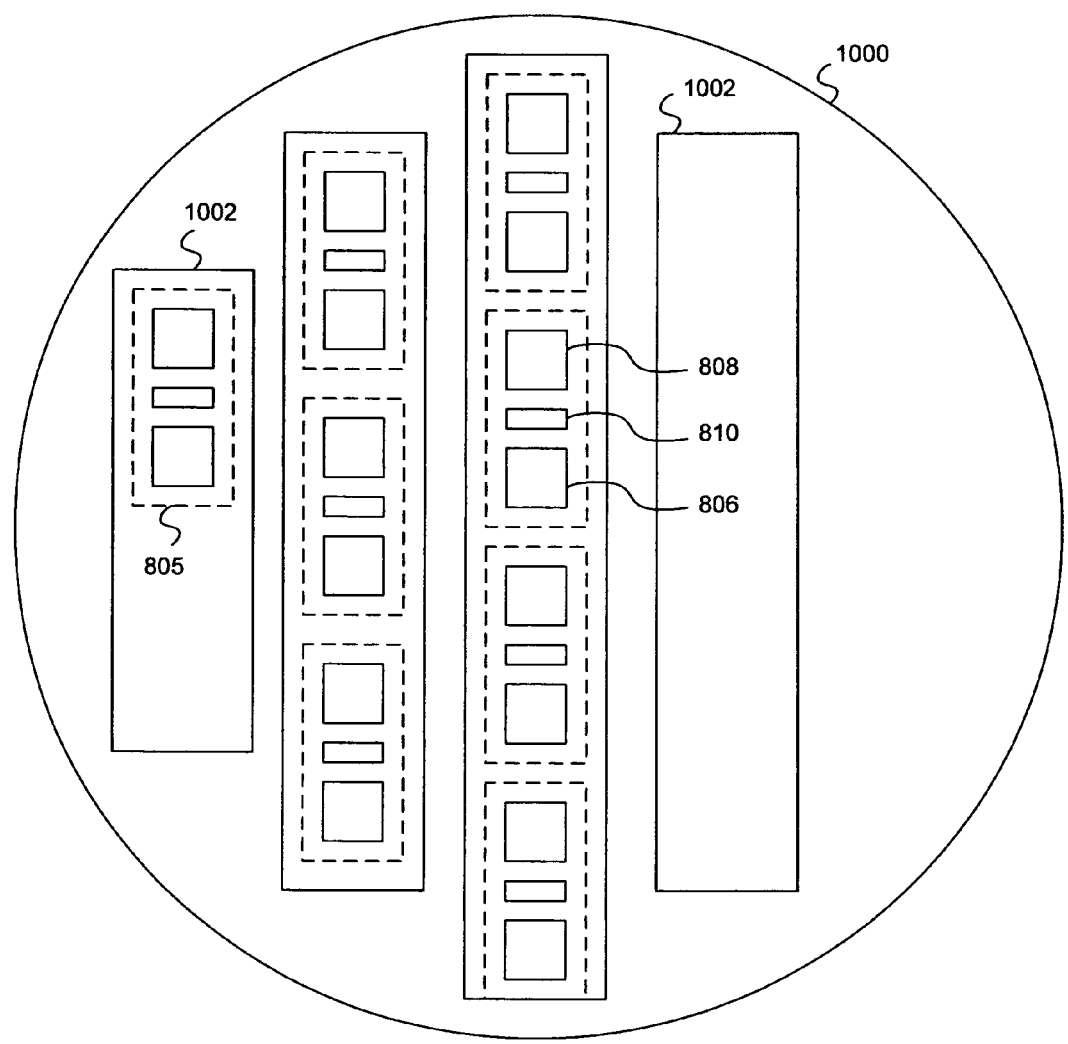
FIG. 10 shows schematically an exemplary silicon wafer according to the present invention.

FIG. 10 shows schematically an exemplary silicon wafer 1000 according to the present invention. Silicon wafer 1000 comprises a plurality of bands 1002. Each band 1002 comprises a plurality of silicon trays 805. Silicon wafer 1000 may comprise hundreds or thousands of silicon trays 805. For example, each silicon tray 805 comprises a first through window 806, a second through window 808, a half-through cavity 810, and trenches 812 (not shown in FIG. 10). It is appreciated that a silicon tray may comprise only one window or more than two windows as well.

Adhesives are properly applied at trenches 812 (see FIG. 8C) for mounting micro-prisms on silicon wafer 1000. Micro-prisms (not shown in FIG. 10) having corresponding lengths are disposed on silicon wafer 1000 and registered with each band 1002. After the micro-prisms are mounted on silicon wafer 1000, the micro-prisms are coated with a thin metal layer through the through windows of the silicon trays. The metal layer on the surface of silicon wafer may be taken away in the following process, or may be left remaining on the surface of the silicon tray. After the coating of micro-prism, silicon wafer 1000 is singulated to form each MPTC comprising a piece of micro-prism mounted on a piece of silicon tray.

Alternatively, the thin metal layer may be coated after the micro-prism and silicon tray are singulated. It is also possible that the micro-prism is first coated with the thin metal layer before mounting on the silicon wafer.

Detected Light Pattern

Figure 11:
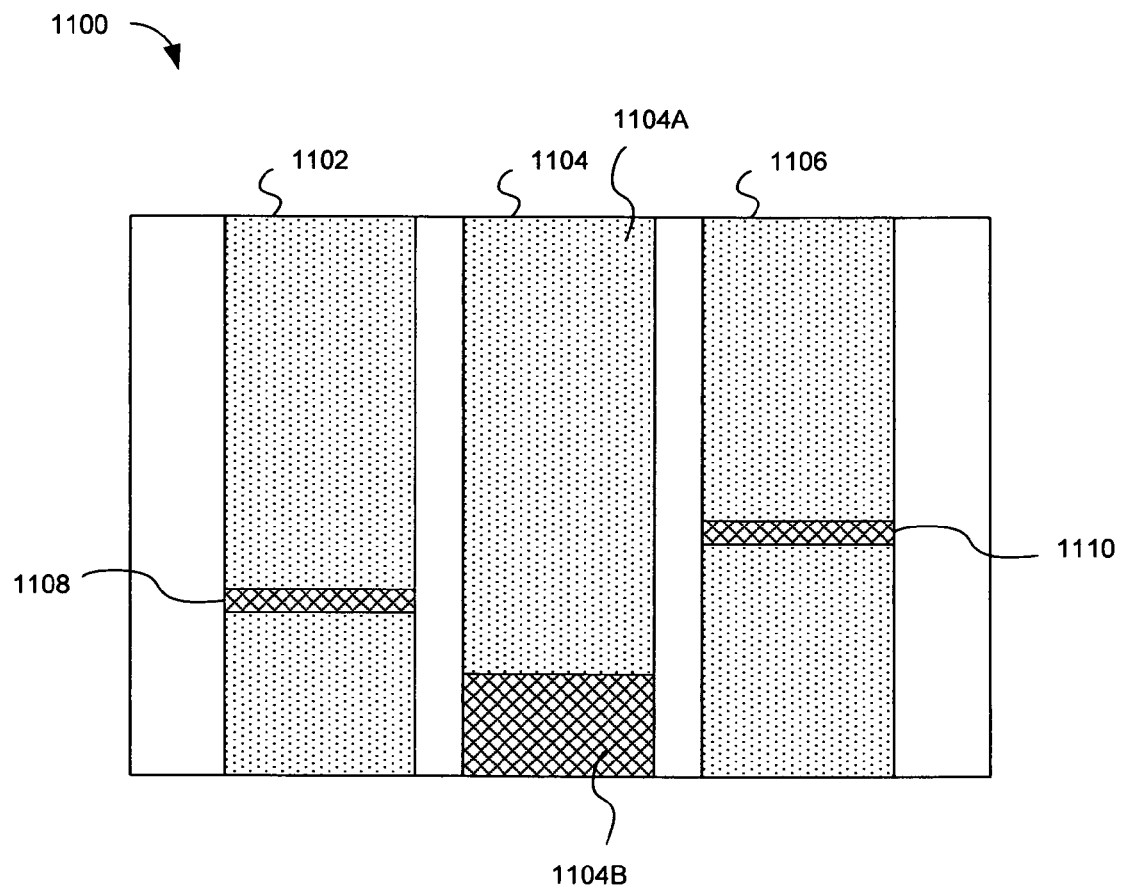
FIG. 11 shows schematically an exemplary light pattern projected on an image sensor from a micro-prism test chip according to the present invention.

FIG. 11 shows an exemplary light pattern 1100 projected on a CMOS 2D image sensor for a MPTC having two through windows, according to the present invention. There are three bands of light 1102, 1104, and 1106. Band 1102 may correspond to the first through window, band 1104 may correspond to the half-through cavity for calibration, and band 1106 may correspond to the second through window. Referring to FIG. 7, the reduced divergence of the emitted laser light by spherical lens 704 may determine the widths of bands 1102, 1104, and 1106. The critical angle is indicated by the boundary of bright part 1104A and dark part 1104B. The resonant angle of the first through window is indicated by a dark bar 1108, and the angle resonant of the second through window is indicated by a dark bar 1110.

While the present invention has been described herein with respect to the exemplary embodiments and the best mode for practicing the invention, it will be apparent to one of ordinary skill in the art that many modifications, improvements and sub-combinations of the various embodiments, adaptations and variations can be made to the invention without departing from the spirit and scope thereof. For the disclosed methods, the steps need not necessarily be performed sequentially.

The terms used in the following claims should not be construed to limit the invention to the specific embodiments disclosed in the specification and the claims. Rather, the scope is to be determined entirely by the following claims, which are to be construed in accordance with established doctrines of claim interpretation. The present specification and figures are accordingly to be regarded as illustrative rather than restrictive.

What is claimed is:

1. An apparatus comprising:
   a disposable micro-prism test chip comprising:
   a micro-tray;
   a micro-prism mounted on the micro-tray, wherein the micro-tray and the micro-prism form at least one cell for providing a fluid dielectric medium for measurement; and
   a thin metal layer coated on a surface of the micro-prism in the at least one cell between the fluid dielectric medium and the micro-prism;
   wherein the micro-tray has at least one through window for forming the at least one cell; and
   wherein only one through window forms a cell.

2. The apparatus of claim 1, wherein the micro-tray has a half-through cavity facing the micro-prism.

3. The apparatus of claim 1, wherein the micro-tray has trenches facing the micro-prism.

4. The apparatus of claim 1, wherein the micro-prism is mounted on the micro-tray using an adhesive.

5. The apparatus of claim 1, wherein the micro-tray is a silicon tray.

6. The apparatus of claim 5, wherein the micro-prism is mounted on the silicon tray before the silicon tray is singulated from the silicon wafer.

7. The apparatus of claim 1, wherein the micro-tray is a plastic molded tray.

8. The apparatus of claim 1, wherein the micro-tray is a metal tray.

9. The apparatus of claim 1, wherein the micro-prism is fabricated by pulling a heated preform, and wherein the preform has the same cross-section as that of the pulled micro-prism.

10. The apparatus of claim 1, wherein the micro-prism is an equilateral triangle having a side less than 5 mm.

11. The apparatus of claim 1, wherein the micro-prism has a length less than 10 mm.

12. The apparatus of claim 1 further comprising
    a laser emitting a transverse mode wave laser light;
    a spherical lens for reducing divergence of the emitted laser light;
    a cylindrical lens for focusing the emitted laser light; and
    a detector for detecting laser light reflected by the surface of the micro-prism wherein the thin metal layer is coated on the surface of the micro-prism.

13. The apparatus of claim 12, wherein the cylindrical lens focuses the emitted laser light at the proximity of the surface of the micro-prism, wherein the thin metal layer is coated on the surface of the micro-prism.

14. The apparatus of claim 12 further comprising a diverging lens between the micro-prism and the detector.

15. The apparatus of claim 1, wherein the thin metal layer is coated on the surface of the micro-prism after the micro-prism is mounted on the micro-tray.

16. The apparatus of claim 1, wherein the thin metal layer is coated on the surface of the micro-prism before the micro-prism is mounted on the micro-tray.

17. The apparatus of claim 1, wherein the thin metal layer is one of a thin gold layer, a thin silver layer, a thin aluminum layer, and a thin copper layer.

* * * * *